(12) United States Patent
Hood

(10) Patent No.: US 6,254,622 B1
(45) Date of Patent: Jul. 3, 2001

(54) BLADE FOR ULTRASONICALLY ASSISTED CUTTING AND HEMOSTASIS

(76) Inventor: Larry Hood, 25652 Nottingham Ct., Laguna Hills, CA (US) 92653-7504

( * ) Notice: Subject to any disclaimer, the term of this patent is extended or adjusted under 35 U.S.C. 154(b) by 672 days.

(21) Appl. No.: 08/910,469

(22) Filed: Jul. 25, 1997

Related U.S. Application Data

(63) Continuation of application No. 08/603,789, filed on Feb. 20, 1996, now abandoned.

(51) Int. Cl.$^7$ .................................................. A61B 17/32
(52) U.S. Cl. ............................................................. 606/169
(58) Field of Search ....................... 606/169, 50; 604/22

(56) References Cited

U.S. PATENT DOCUMENTS

| | | |
|---|---|---|
| 3,086,288 | 4/1963 | Balamuth et al. . |
| 4,931,047 * | 6/1990 | Broadwin et al. ............... 606/169 X |
| 5,176,677 * | 1/1993 | Wuchinich ....................... 606/169 X |
| 5,207,675 * | 5/1993 | Canady ............................... 606/37 X |
| 5,261,922 | 11/1993 | Hood . |
| 5,281,216 * | 1/1994 | Klicer ................................... 606/50 X |
| 5,324,299 | 6/1994 | Davison et al. . |
| 5,391,144 * | 2/1995 | Sakurai et al. .................... 606/169 X |
| 5,562,610 * | 10/1996 | Brumbach ........................ 606/169 X |

FOREIGN PATENT DOCUMENTS

014708 * 8/1993 (WO) .................................... 606/169

* cited by examiner

*Primary Examiner*—Michael H. Thaler
(74) *Attorney, Agent, or Firm*—Irell & Manella, LLP.

(57) ABSTRACT

An ultrasonically driven surgical blade which has a recessed cutting portion that extends to a pointed tip. The interface between the tip and the recessed cutting portion provides a cutting edge which has a relatively low attack angle. The recessed cutting portion is located on only one side of the blade to create an unsymmetrical cutting action. When the surgical blade is ultrasonically driven, the unsymmetrical cutting surface and the offset center of gravity creates a transverse movement of the blade. The transverse movement of the blade more efficiently transfers the ultrasonic energy to the tissue to increase tissue coagulation. The blade may be driven by an acoustic wave that has a first base frequency that is modulated by, or switched with, a second frequency to further improve hemostasis. The blade may be coupled to a horn by a sleeve that contains electro-cautery pins, and/or lumens that provide gas for an argon plasma, or a pressure or vacuum source. The profile of the blade tip is no larger than the profile of the blade body so that the blade can be easily inserted into an instrument such as a trocar sleeve.

5 Claims, 3 Drawing Sheets

HIGH FREQUENCY MODULATION

FREQUENCY SWITCHING

BLADE FOR ULTRASONICALLY ASSISTED CUTTING AND HEMOSTASIS

This is a Continuation Application of application Ser. No. 08/603,789, filed Feb. 20, 1996 now abandoned.

BACKGROUND OF THE INVENTION

1. Field of the Invention

The present invention relates to an ultrasonically driven surgical blade.

2. Description of Related Art

Ultrasonic knives are commonly used to cut and coagulate tissue. An ultrasonic knife assembly includes a blade that is coupled to an ultrasonic horn. The horn contains a transducer that is excited by an electrical source. The excitation of the transducer induces a corresponding vibratory movement of the blade. It has been found that the vibratory movement of the blade can increase the cutting and/or coagulation of tissue. Generally speaking, a sharp blade will increase the cutting efficiency of the knife, while a dull blade has been found to improve hemostasis.

U.S. Pat. No. 5,324,299 issued to Davison et al. discloses an ultrasonic blade which has a hook. The hook has a sharpened blade recess which terminates into a dull tip. The dull tip tends to grab and pull the patient tissue into tension, so that the sharp blade portion can more readily cut the tissue. Although potentially effective in cutting unsupported fatty tissue, the Davison blade would be relatively ineffective in cutting non-hydrogenous tissue.

U.S. Pat. No. 3,086,288 issued to Balamuth et al., discloses an arcuate shaped surgical blade which has a cutting surface that extends from the base of the blade to the blade tip. Although potentially efficient in cutting tissue, the sharpness of the entire blade works against coagulation. Additionally, the wide profile of the Balamuth blade does not allow the knife to be inserted into a trocar, thereby limiting the use of the blade in laparoscopic procedures. It would be desirable to provide a low profile ultrasonically driven blade that is efficient in both cutting and coagulating tissue, and has a profile that allows the knife to be inserted through a trocar.

SUMMARY OF THE INVENTION

The present invention is an ultrasonically driven surgical blade which has a recessed cutting portion that extends to a pointed tip. The interface between the tip and the recessed cutting portion provides a cutting edge which has a relatively low attack angle. The recessed cutting portion is located on only one side of the blade to create an unsymmetrical cutting action. When the surgical blade is ultrasonically driven, the unsymmetrical cutting surface and the offset center of gravity creates a transverse movement of the blade. The transverse movement of the blade more efficiently transfers the ultrasonic energy to the tissue to increase tissue coagulation. The blade may be driven by an acoustic wave that has a first base frequency that is modulated by, or switched with, a second frequency to further improve hemostasis. The blade may be coupled to a horn by a sleeve that contains electro-cautery pins, and/or lumens that provide gas for an argon plasma, or a pressure or vacuum source. The profile of the blade tip is no larger than the profile of the blade body so that the blade can be easily inserted into an instrument such as a trocar sleeve.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 3:
FIG. 3 is an end view of the surgical blade.
Figure 1:
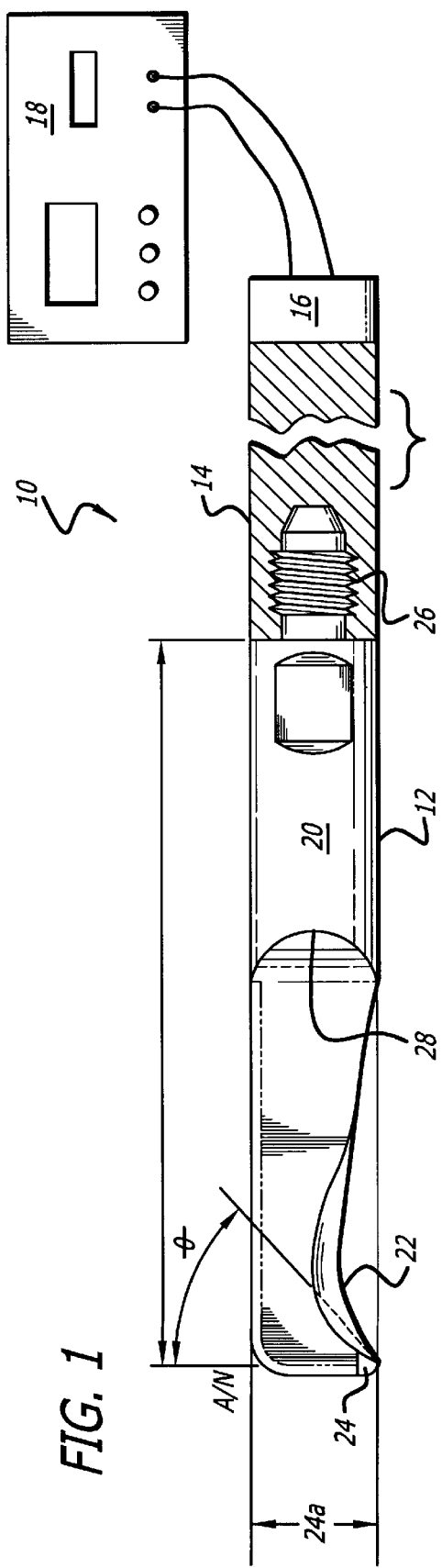
FIG. 1 is a side view of a surgical blade assembly of the present invention.
Figure 2:
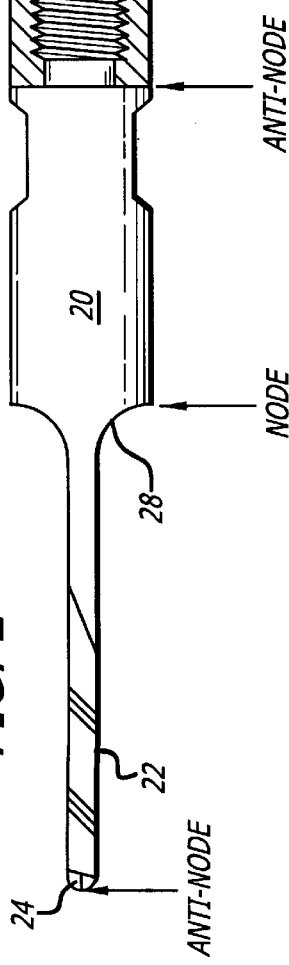
FIG. 2 is a bottom view of the surgical blade.

Referring to the drawings more particularly by reference numbers, FIGS. 1–3 show a surgical knife assembly 10 of the present invention. The assembly is typically used to cut the tissue of a human patient. The knife assembly 10 includes a blade 12 that is coupled to an extender 14. The extender 14 is coupled to an ultrasonic horn schematically depicted as element 16. The horn 16 typically contains a transducer that converts an electrical signal into a mechanical movement of the extender 14 and the blade 12. The ultrasonic horn 16 is connected to an electronic controller 18 which provides an electrical signal that drives the blade 12.

The blade 12 includes a body 20 which has a recessed cutting portion 22 that extends to a pointed tip 24. The interface between the tip 24 and the recessed portion 22 define a cutting edge which has an attack angle θ. The blade 12 has a relatively low attack angle that creates an efficient cutting action of the blade. In the preferred embodiment, the attack angle θ is approximately 45°. The pointed tip 24 assists in the cutting action of the blade. The low attack angle and pointed tip provide a surgical blade that can effectively cut both hydrogenous tissue and non-hydrogenous tissue without requiring tension on the cutting medium.

The tip profile 24a has a length that extends across the width of the blade 12. The tip width is no wider than the diameter of the blade body 20. Maintaining the entire profile of the tip within the envelope of the blade body provides a blade profile which can be readily inserted into and withdrawn from a surgical instrument such as a trocar sheath. Insertion of the blade through a trocar sheath allows the surgeon to use the assembly in procedures such as laparoscopy.

The sharp recessed cutting surface 22 is preferably located on only one side of the blade 12. Placing the cutting surface on only one side of the blade creates an unsymmetrical cutting action of the knife. The unsymmetrical cutting surface also creates a center of gravity that is offset from the dimensional centerline of the blade body 20. The unsymmetrical cutting force and the offset center of gravity will induce a transverse movement of the blade (perpendicular to the longitudinal axis of the blade) when the blade is ultrasonically excited. The transverse movement of the surgical blade will cause the dull side of the blade to strike the tissue. It has been found that ultrasonic energy increases hemostasis. The transverse movement of the blade provides an efficient means of transferring the ultrasonic energy directly into the tissue. Additionally, the transverse movement of the blade will also move the blood away from the cutting edge and again allow a more efficient transfer of ultrasonic energy to the tissue.

The blade 12 has an end 26 opposite from the tip 24 that is attached to the extender 14. In the preferred embodiment, the end 26 is threaded and screwed into corresponding threads of the extender 14. The base of the blade threads is preferably located at an anti-node location of the assembly 10. The tip 24 is also preferably located at an anti-node location. In the preferred embodiment, the blade 12 has a step 28 located at a node location of the assembly 10. The radius of the step 28 is preferably one-half of the cutting surface 22 thickness. As shown in FIG. 2, the recessed cutting portion 22 also has a gradual tapered area. The combination of the nodal step 28 and the gradual taper from the node to the anti-node tip provides a blade 12 which has a relatively high gain and sufficient structural integrity for operation of the blade 12 at high excitation frequencies, and excursions.

Figure 4:
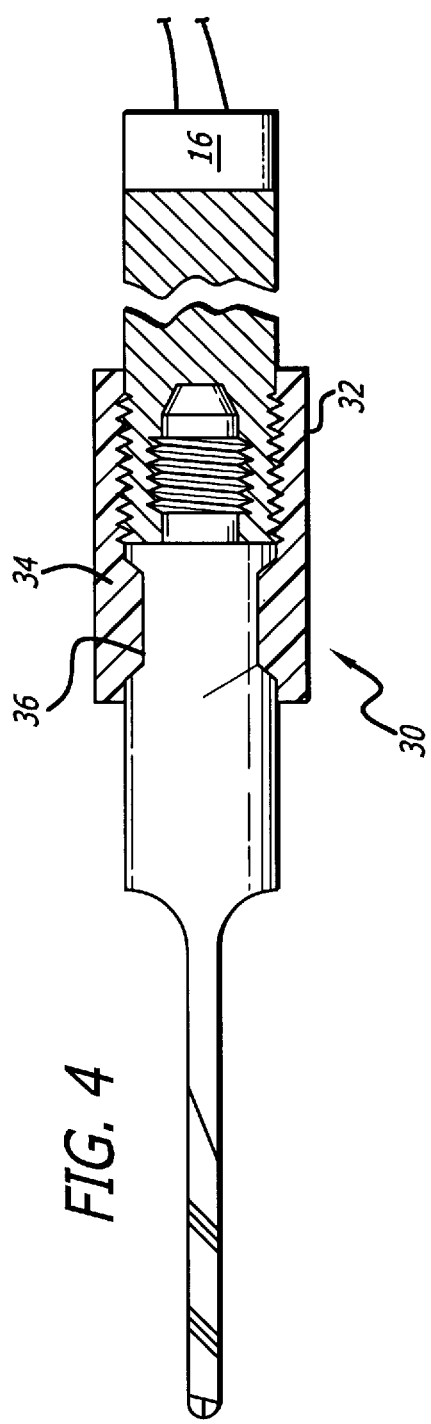
FIG. 4 is a bottom view of the surgical blade with a sleeve.

As shown in FIG. 4, the assembly may have a sleeve 30 that prevents the blade body 12 or extender 14 from making contact with a trocar sleeve or non-target tissue. The sleeve 30 may be constructed from an insulative housing 32 which has a pair of spring fingers 34 that snap into corresponding grooves or wrench flats 36 of the blade body 12.

Figure 5:
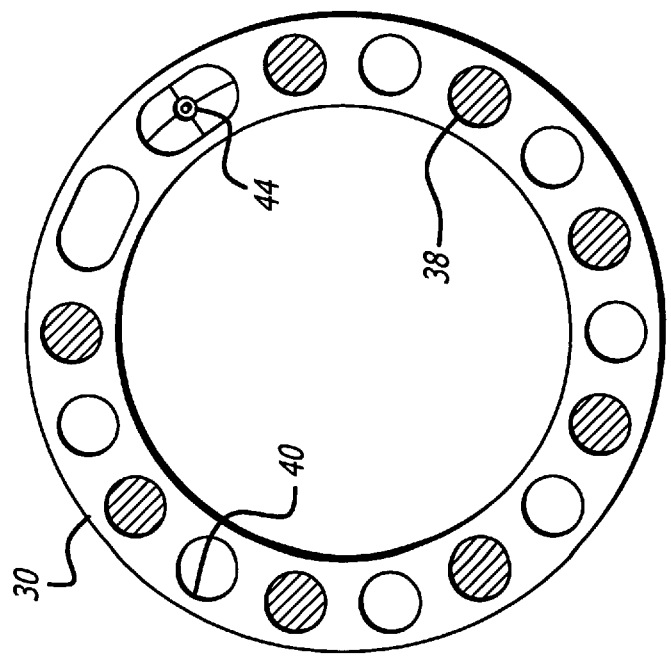
FIG. 5 is a cross-sectional view of the sleeve.

As shown in FIG. 5, the sleeve 30 may have a plurality of pins 38 and a plurality of lumens 40. The pins 38 may be connected to a voltage source of the controller 18 which applies a radio frequency voltage across alternate pins 38, and/or between the pins 38 and the blade 12. The voltage will create an electro-cautery effect that assists the coagulation of tissue. The lumens 40 may be coupled to a source of pressurized gas 43 or liquid to blow blood, debris, etc., out of the path of the knife. Some of the lumens 40 may be coupled to an aspirator. One or more of the lumens 42 may also contain a needle 44 and be coupled to a argon gas supply to create an argon beam coagulator. The combination of the low profile blade and the electro-cautery, pressurized gas, argon beam coagulator provides an assembly that can be inserted into a trocar and provide a variety of functions such as cutting, coagulating, cleaning, etc. Although the electro-cautery, pressurized gas and argon coagulator functions are shown together in one sleeve, it is to be understood that any one function, or combination of functions can be incorporated into the sleeve 30.

Figure 6A:
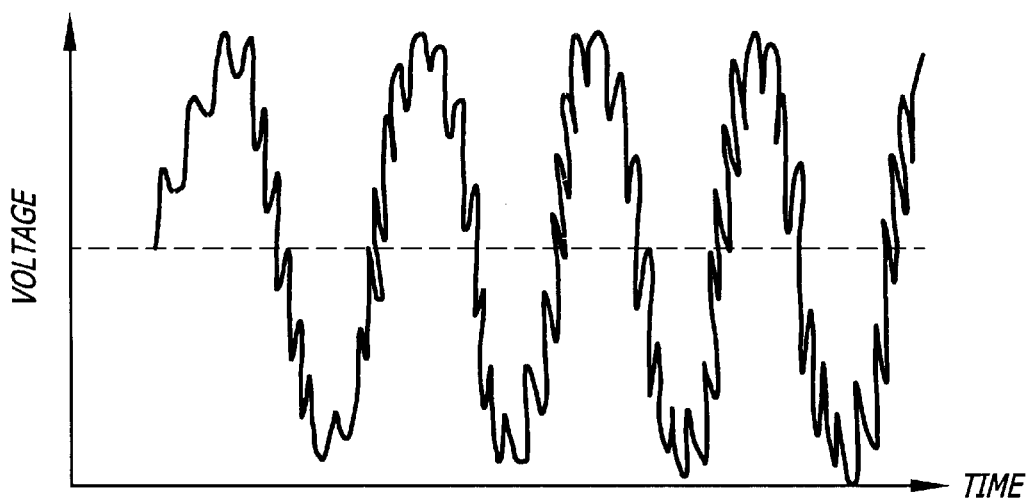
FIG. 6a is a graph showing the waveform of a modulated acoustic wave that drives the surgical blade.
Figure 6B:
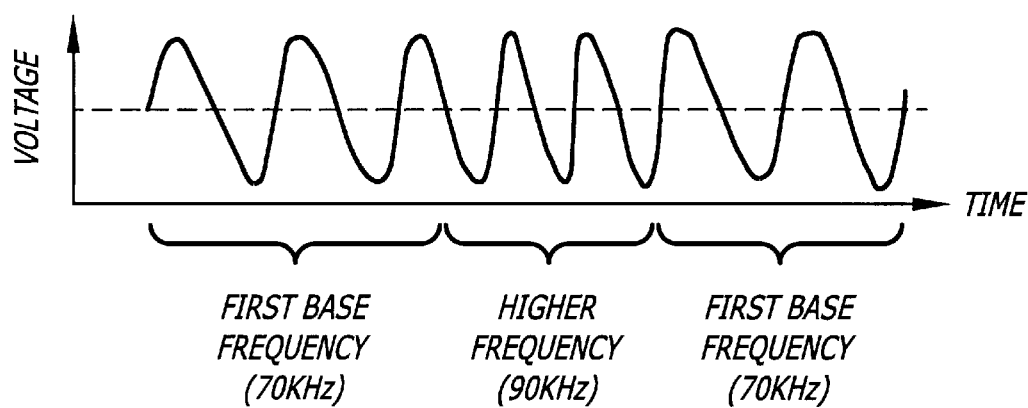
FIG. 6b is a graph showing a waveform that has a first frequency which is switched with a second frequency.

FIGS. 6a and 6b show waveforms of an acoustic wave that drives the blade 12. Generally speaking a higher wave frequency will increase the hemostatic effect and decrease the cavitation effect of the knife. Cavitation tends to atomize the blood, thereby decreasing visibility.

The upper acoustic wave frequency is limited by the anti-nodal location of the blade. A high driving frequency that does not correspond to the dimensions of the blade may create undesirable stress and heat within the knife. To obtain the advantages of a higher driving frequency, a relatively low base wave frequency can be either modulated with a higher frequency as shown in FIG. 6a, or switched with a higher frequency as shown in FIG. 6b. In this manner, a blade assembly and dimensions that correspond to the first base frequency can be excited with a higher frequency without generating undesirable stress and heat. Additionally, the nodal step and the tapered cutting portion provide a blade configuration that provides enough structural integrity to withstand the additional stress generated by the higher frequency. The acoustic wave frequency typically ranges from 60,000–120,000 hertz (Hz). In the preferred embodiment, the first base frequency is 70 KHz and the second frequency is 90 KHz.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An ultrasonic cutting blade, comprising:
a body which has a diameter, said body has a stepped flat portion which has a first side and a second side, said stepped flat portion has a recessed cutting portion located on only said first side of said body and which terminates at a pointed tip at an outermost distal end of said body, said stepped flat portion having a width that is no greater than said diameter of said body.

2. The cutting blade as recited in claim 1, wherein said tip has a profile that is no greater than a profile of said body.

3. The cutting blade as recited in claim 1, wherein said recessed cutting portion and said tip form an oblique cutting edge that is at an attack angle relative to a longitudinal axis of said body.

4. The cutting blade as recited in claim 3, wherein said attack angle is approximately 45°.

5. The cutting blade as recited in claim 1, wherein said body has a center of gravity that is offset from a centerline of said body.

* * * * *